US005720952A

United States Patent [19]
Clark et al.

[11] Patent Number: 5,720,952
[45] Date of Patent: Feb. 24, 1998

[54] METHOD OF TREATING MYELO-SUPPRESSION WITH GM-CSF

[75] Inventors: Steven C. Clark, Winchester; Randal J. Kaufman, Boston; Gordon C. Wong, Cambridge, all of Mass.

[73] Assignee: Novartis Corporation, Basel, Switzerland

[21] Appl. No.: 472,022

[22] Filed: Jun. 6, 1995

Related U.S. Application Data

[60] Division of Ser. No. 652,447, Sep. 19, 1984, which is a continuation-in-part of Ser. No. 628,342, Jul. 6, 1984, abandoned.

[51] Int. Cl.$^6$ .............................. A61K 38/19; C07K 14/52
[52] U.S. Cl. .................. 424/85.1; 424/184.1; 424/198.1; 514/2; 514/8; 514/12; 514/885
[58] Field of Search ............................ 514/2, 8, 12, 885; 424/85.1, 85.2, 184.1

[56] References Cited

U.S. PATENT DOCUMENTS

| | | | |
|---|---|---|---|
| 5,078,996 | 1/1992 | Conlon et al. | 424/85.1 |
| 5,147,799 | 9/1992 | Bursuker et al. | 435/240.1 |

OTHER PUBLICATIONS

Wing et al. (1982) J. Clin. Invest. vol. 69, pp. 270–276.
Lusis et al. (1980) Proc. Natl. Acad. Sci. U.S.A. vol. 77, No. 9, pp. 5346–5350.
Yunis, et al., FEBS Letters, 1978, 90: 279–82.
Wu, et al. J. Biol. Chem., 1979, 254: 6226–28.
Gasson, et al. Science, 1984, 226: 1339–1342.
Fojo, et al., Biochemistry, 1978, 17: 3109–16.
Lusis, et al., Blood, 1981, 57: 13–21.
Nicola, et al., Blood, 1979, 54: 614–27.
Fojo, et al., Biophys. Acts., 1977, 494: 92–99.
Price, et al., Biochem. J., 1975, 148: 209–17.
Metcalf, The Hemopoietic Colony Stimulating Factors, Elsevier (1984), pp. 81–84, 215–227, 309–329.
Cohen (1995) Science vol. 270 p. 908.

*Primary Examiner*—John Ulm
*Assistant Examiner*—Prema Mertz
*Attorney, Agent, or Firm*—Fitzpatrick, Cella, Harper & Scinto

[57] ABSTRACT

A method for preparing and isolating a transformation vector containing CSF/cDNA is described. The method comprises:

preparing RNA from a cell that produces CSF;

preparing polyadenylated messenger RNA from the RNA;

preparing single stranded cDNA from the messenger RNA;

converting the single stranded cDNA to double stranded cDNA;

inserting the double stranded cDNA into transformation vectors and transforming bacteria with the vector to form colonies;

picking pools of 200 to 500 colonies each and isolating plasmid DNA from each pool;

transfecting the plasmid DNA into suitable host cells for expressing CSF protein;

culturing the transfected cells and assaying the supernatant for CSF activity; and selecting CSF positive pools and screening the colonies used to make the pool to identify a colony having CSF activity. Also described are a cDNA coding for a protein having CSF activity (i.e. CSF/cDNA), a microorganism or cell line transformed with a recombinant vector containing such CSF/cDNA, and a method for producing CSF protein by expressing said CSF/cDNA by culturing a microorganism or cell line.

4 Claims, 4 Drawing Sheets

```
                    10                          30                           45
GAATTCCGCT  GGAGG ATG TGG CTG CAG AGC CTG CTG CTC TTG GGC ACT GTG GCC TGC
                  MET Trp Leu Gln Ser Leu Leu Leu Leu Gly Thr Val Ala Cys 60                75                      90                      150
                   Ala                             Thr
                   G                               C
AGC ATC TCT GCA CCC TCC CGC TCG CCC AGC CCC AGC AGG CAG CCC TGG GAG CAT
Ser Ile Ser Ala Pro Ser Arg Ser Pro Ser Pro Ser Arg Gln Pro Trp Glu His 120                 135             150                      165
GTG AAT GCC ATC CAG GAG GCC CGG CGT CTC CTG AAC CTG AGT AGA GAC ACT GCT
Val Asn Ala Ile Gln Glu Ala Arg Arg Leu Leu Asn Leu Ser Arg Asp Thr Ala 180                 195                 210
        MET                               Ile
        G                                 A
GCT GAG ATA AAT GAA ACA GTA GAA GTC GTC TCA GAA ATG TTT GAC CTC CAG GAG
Ala Glu Ile Asn Glu Thr Val Glu Val Val Ser Glu MET Phe Asp Leu Gln Glu 225                 240                 255                 270
                                                                   G       C
CCG ACC TGC CTA CAG ACC CGC CTG GAG CTG TAC AAG CAG GGC CTG CAG GGC AGT
Pro Thr Cys Leu Gln Thr Arg Leu Glu Leu Tyr Lys Gln Gly Leu Arg Gly Ser 285             300                 315
CTC ACC AAG CTC AAG GGC CCC TTG ACC ATG ATG GCC AGC CAC TAC AAG CAG CAC
Leu Thr Lys Leu Lys Gly Pro Leu Thr MET MET Ala Ser His Tyr Lys Gln His 330             345             360                 375
                                            Thr
             G       T                      C
TGC CCT CCA ACC CCA GAA ACG TCC TGT GCA ACC CAG ATT ATC ACC TTT GAA AGT
Cys Pro Pro Thr Pro Glu Thr Ser Cys Ala Thr Gln Ile Ile Thr Phe Glu Ser 390                 405                 420                 435
                                            Ile
                                            T
TTC AAA GAG AAC CTG AAG GAC TTT CTG CTT GTC ACC CCC TTT GAC TGC TGG GAG
Phe Lys Glu Asn Leu Lys Asp Phe Leu Leu Val Thr Pro Phe Asp Cys Trp Glu 450         460     470     480     490         500
       Glu
       A
CCA GTC CAG GGG TGA GACCGGCCAG ATGAGGCTGG CCAAGCCGGG GAGCTGCTCT CTCATGAAAC
Pro Val Gln Gly *

510         520         530         540         550         560         570
       A                                   G                                   G
AAGAGCTGGA AACTCAGGAT GGTCATCTTG CAGGGACCAA GGGGTGGGCC ACATCCATGG TGGGAGTGGC
      580         590         600         610         620         630         640
 T
CGGGACCTGC CCTGGGCCAC ACTGACCCTG ATACAGGCAT GGCAGAAGAA TGGGAATATT TTATACTGAC
      650         660         670         680         690         700         710
AGAAATCAGT AATATTTATA TATTTATATT TTTAAAATAT TTATTTATTT ATTTATTTAA GTTCATATTC
      720         730         740         750         760         770         780
CATATTTATT CAAGATGTTT TACCGTAATA ATTATTATTA AAAATATGCT TCTAAAAAAA AAAAAAAAAA
```

METHOD OF TREATING MYELO-SUPPRESSION WITH GM-CSF

This is a division of application Ser. No. 06/652,447, filed Sep. 19, 1984, which in turn is a continuation-in-part of application Ser. No. 06/628,342, filed Jul. 6, 1984, now abandoned.

FIELD OF THE INVENTION

This invention relates to the discovery and production of a protein having the ability to stimulate the growth and differentiation of primate hematopoietic progenitor cells, and particularly to vectors containing the gene for expressing said protein, microorganisms and cell lines transformed with said vectors, and methods for producing said protein by recombinant DNA techniques.

BACKGROUND OF THE INVENTION

The many different cell types found in blood are all derived from pluripotent hematopoietic stem cells. Stem cells perform two functions: (1) they reproduce themselves, thereby maintaining a stem cell population in the body and (2) they provide progeny cells committed to differentiate into any of the mature blood cell types. The cell which is committed to differentiate along a particular hematopoietic pathway is termed a progenitor cell. Progenitor cells for T lymphocytes, B lymphocytes, granulocytes, red blood cells, platelets, and eosinophils, as well as earlier progenitors which can individually give rise to several of the mature cell types, have been studied experimentally both in vivo and in vitro (Dexter, T. M. 1983 J. Pathology 141 415–433). It has been determined in vitro that proliferation and/or differentiation of each progenitor cell type depends upon specific "factors" which have been derived from various sources. For example, the later progenitors of red blood cells require a factor called erythropoietin. The factors required for survival, proliferation and differentiation of the myeloid progenitors committed to form mature neutrophilic granulocytes, monocytes and mature macrophages are called colony stimulating factors (CSFs).

CSF activity has been studied extensively in the mouse. Most adult mouse organs produce CSF activity. However, compositions containing CSF activity that have been obtained from various tissues and by various methods appear to differ in their biochemical characteristics. Thus, the structural relationships between the different factors remain unknown. Furthermore, CSF activity appears to act at more than one step of granulocyte and macrophage development, and again it has been uncertain whether a single factor is responsible for all of the observed activities or whether a different factor acts at each step (Burgess, A. and Metcalf, D. 1980 Blood 56 947–957).

Human CSF activity has been obtained from placenta, certain fetal tissues, macrophages, and stimulated T cells. A line of T cells (Mo) that produces one or more potent CSF activities was established from a patient with a T cell variant of hairy cell leukaemia (leukaemic reticuloendotheliosis) (Golde et al 1978 Blood 52 1068–1072).

The ability of CSF activity to stimulate granulocyte and macrophage production indicates that pharmaceutical compositions having CSF activity are clinically useful in situations where increased production of these (myeloid) cell types is required. Indeed, several patients with extremely high levels of apparently normal circulating granulocytes have been shown to have tumors which over-produce CSFs. In one case, upon surgical removal of the tumor, the granulocyte count rapidly declined towards a normal level, strongly suggesting that CSFs may be useful in regulating the numbers of circulating granulocytes (Hocking, W. Goodman J. and Golde, D. Blood 61 600 (1983)). In particular, CSF compositions are useful clinically for the treatment of myelo-suppression caused by chemotherapeutical or irradiation treatment of cancer. In addition, CSF compositions are useful in treating severe infections because CSF can increase and/or activate the number of granulocytes and/or monocytes.

Biological and biochemical characterization of compositions having CSF activity, and study of these compositions in the clinical setting have been hampered to date by the scarcity and impurity of human and/or other primate CSF compositions. It can be appreciated that it would be desirable to identify the protein or proteins responsible for CSF activity. Furthermore, it would be desirable to have a primate, preferably human, source of such CSF activity that could readily supply these proteins in quantities and purity sufficient for biological and biochemical characterization and for use as therapeutic agents.

Recently developed techniques of molecular cloning make it possible to clone a nucleotide sequence which encodes a protein and to produce that protein in quantity using a suitable host-vector system (Maniatis, T. *Molecular Cloning—A Laboratory Manual* Cold Spring Harbor Laboratory, Cold Spring Harbor, N.Y. 1982). The protein can then be recovered by known separation and purification techniques. Cloning methods which have been used to date can be grouped into three general categories: (1) methods based upon knowledge of the protein structure, for example, its amino acid sequence; (2) methods based upon identification of the protein expressed by the cloned gene using an antibody specific for that protein; and (3) methods based upon identification of an RNA species which can be translated to yield the protein or activity encoded by the gene of interest.

Each of these classes of methods becomes difficult to apply when the protein of interest, such as CSF protein, is produced in very low amount. Thus, if it is difficult to obtain an adequate quantity of purified protein, then it is difficult to determine the amino acid sequence of the protein. Similarly, identification of an expressed protein by antibody binding is preferentially carried out using a high-titer monospecific polyclonal antiserum. Such an antiserum cannot be obtained in the absence of quantities of the pure protein (antigen). A monoclonal antibody offers an alternative approach, but the required antibody can also be difficult to obtain in the absence of suitable antigen, and such monoclonal antibody may not react with the protein in the form in which the protein is expressed by available recombinant host-vector systems. Finally, translation of an RNA species to yield an identifiable protein or activity requires that the RNA in question be present in the RNA source in sufficient abundance to give a reliable protein or activity signal. The relative abundance of an RNA encoding a particular protein generally parallels the abundance of the protein, so that a rare protein is usually encoded by a rare mRNA.

The Mo cell line has been used both as a starting material for purifying human CSFs and for identifying the corresponding messenger RNAs. However, even with this relatively good source of CSF activity, it has proved to be extremely difficult to isolate enough of the protein for structural studies.

In order to overcome the problems inherent in cloning the nucleotide sequence encoding a rare protein such as CSF by the methods described above, a novel method was developed. This method requires only that the gene product or its activity can be reliably measured.

SUMMARY OF THE INVENTION

The present invention overcomes the problems of the prior art and provides a ready source of protein having CSF activity using recombinant DNA technology. In accord with the present invention, a novel cloning technique that requires only an assay for CSF activity is utilized to clone cDNA coding for a protein having CSF activity. Thus, the present invention provides a cDNA coding for a protein having CSF activity (i.e. CSF/cDNA), a microorganism or cell line transformed with a recombinant vector containing such CSF/cDNA, and a method for producing CSF protein by expressing said CSF/cDNA by culturing a microorganism or cell line. Because the CSF protein is produced from a clone in accord with the present invention, we can be sure that it is a protein that has CSF activity. The invention further comprises a method for preparing and isolating a transformation vector containing CSF/cDNA, said method comprising:

preparing RNA from a cell that produces CSF;

preparing polyadenylated messenger RNA from said RNA;

preparing single stranded cDNA from said messenger RNA;

converting the single stranded cDNA to double stranded cDNA;

inserting the double stranded cDNA into transformation vectors and transforming bacteria with said vector to form colonies;

picking pools of 200 to 500 colonies each and isolating plasmid DNA from each pool;

transfecting the plasmid DNA into suitable host cells for expressing CSF protein;

culturing the transfected cells and assaying the supernatant for CSF activity; and selecting CSF positive pools and screening the colonies used to make the pool to identify a colony having CSF activity.

The CSF proteins of this invention are growth and differentiation hormones for the cells of the myeloid system. They are useful clinically for the treatment of myelosuppression especially (sympotomatic) granulocyto-penia following chemotherapeutical or irradiation treatment of cancer.

BRIEF DESCRIPTION OF THE DRAWINGS

FIG. 1 illustrates DNA sequences that code for a CSF protein in accord with the present invention. The full DNA sequence codes for human CSF. The changes illustrated above for the human sequence are for differences in the DNA sequence coding for gibbon CSF. Deduced amino acid sequences are also illustrated.

DETAILED DESCRIPTION OF THE INVENTION

The following definitions are supplied in order to facilitate the understanding of this case. To the extent that the definitions vary from meaning circulating within the art, the definitions below are to control.

Amplification means the process by which cells produce gene repeats within their chromosomal DNA.

CSF is a biological activity defined by the assays as described herein.

CSF protein is a protein from a primate source that exhibits CSF activity. For purposes of the present invention the term CSF protein includes modified CSF protein, alleleic variations of CSF protein, and CSF protein preceded by a MET residue.

Downstream means the direction going towards the 3' end of a nucleotide sequence.

An enhancer is a nucleotide sequence that can potentiate the transcription of a gene independent of the position of the enhancer in relation to the gene or the orientation of the sequence.

A gene is a deoxyribonucleotide sequence coding for a given protein. For the purposes herein, a gene shall not include untranslated flanking regions such as RNA transcription initiation signals, polyadenylation addition sites, promoters or enhancers.

Ligation is the process of forming a phosphodiester bond between the 5' and 3' ends of two DNA strands. This may be accomplished by several well known enzymatic techniques, including blunt end ligation by T4 ligase.

Orientation refers to the order of nucleotides in a DNA sequence. An inverted orientation of a DNA sequence is one in which the 5' to 3' order of the sequence in relation to another sequence is reversed when compared to a point of reference in the DNA from which the sequence was obtained. Such points of reference can include the direction of transcription of other specified DNA sequences in the source DNA or the origin of replication of replicable vectors containing the sequence.

Transcription means the synthesis of RNA from a DNA template.

Transformation means changing a cell's genotype by the cellular uptake of exogenous DNA. Transformation may be detected in some cases by an alteration in cell phenotype. Transformed cells are called transformants. Pre-transformation cells are referred to as parental cells.

Translation means the synthesis of a polypeptide from messenger RNA.

Colony-stimulating factor activity (CSF) can be derived from a number of cellular sources including conditioned medium from peripheral blood mononuclear cells, lung and placental tissue, and bone marrow, urine from anemic patients, serum, and normal and neoplastic cells of T-lymphocyte and mononuclear phagocyte lineage. One cell line that produces CSF is the Mo cell line. The CSF produced by this cell line is known as granulocyte-macrophage CSF (or GM-CSF).

In order to isolate a CSF clone in accord with the present invention, a novel procedure was used that requires only an assay technique for CSF activity. First, a cell that produces CSF activity such as T-lymphocyte cells (or other sources such as set forth above) is identified. The mRNA of the cell is then harvested. Preferably, T-lymphocyte cells are used. In such case the membrane bound mRNA, which contains the mRNA for lymphokines, is separated from free mRNA in the cells. This separation is believed to enrich the collected mRNA 5–10 times for lymphokine sequences and thus reduces the effort involved in identifying the desired CSF clone. Polyadenylated messenger RNA is then prepared by chromatography on oligo dT cellulose.

A cDNA library is prepared from the mRNA using a vector suitable for transfection into a host to express the desired protein having CSF activity. First strand cDNA is prepared using standard methods using the mRNA prepared above. The RNA/cDNA hybrid is then converted to double-stranded cDNA form. The cDNA can then be inserted into a suitable vector.

The preferred host-vector system for the isolation of a CSF clone is based on expression of the CSF cDNA in a suitable transformation vector. A suitable transformation vector can rely on the transient introduction of DNA into mammalian cells (Mellon, P., V. Parker, Y. Gluzman, T. Maniatis 1981 Cell 27 279-288). In order to isolate the desired CSF transformants, it is not required that all cells of the population stably contain exogenous genes that express the desired CSF product. It is possible to transiently introduce exogenous genes into a subpopulation of cells such that the subpopulation will express the desired product over a period of several days. Because a selectable marker is not required in the transformation vector for the DNA transfection and expression system in accord with the present invention, the exogenous DNA can be lost upon growth of the cells over a 1–2 week period. However, 2–3 days after transfection of suitable mammalian cells, the desired products are found to be synthesized and can be detected.

The host-vector system of choice is based on the development of CV-1 monkey cell lines transformed with a replication-origin-defective SV40 DNA molecule (Gluzman, Y., Cell 23 175–182, 1981). The transformed monkey CV-1 cells containing defective SV40 DNA, designated COS (CV-1, origin defective, SV40), do not contain a complete copy of the SV40 genome, but produce high levels of large T antigen and are permissive for SV40 DNA replication. They also efficiently support the replication of SV40 containing deletions in the early region and of bacterial plasmids which contain the SV40 origin of replication (Myers, R. M. & Tjian, R. 1980 PNAS 77 6491–6495). Thus, this system provides a means of amplifying transfected exogenous DNA via SV40 mediated DNA replication in order to increase the level of mRNA and protein expressed from the exogenous DNA. However, other similar systems are also useful.

Vectors used for CSF expression typically contain various elements such as enhancers, promoters, introns, polyadenylation sites, 3' noncoding regions and translational activators as will be described below.

The vectors herein may include enhancers. Enhancers are functionally distinct from promoters, but appear to operate in concert with promoters. Their function on the cellular level is not well understood, but their unique characteristic is the ability to activate or potentiate transcription without being position or orientation dependent. Promoters need to be upstream of the gene, while enhancers may be present upstream or 5' from the promoter, within the gene as an intron, or downstream from the gene between the gene and a polyadenylation site or 3' from the polyadenylation site. Inverted promoters are not functional, but inverted enhancers are. Enhancers are cis-acting, i.e., they have an effect on promoters only if they are present on the same DNA strand. For a general discussion of enhancers see Khoury et al., Cell 33:313–314 (1983).

Preferred enhancers for use with mammalian cells are obtained from animal viruses such as simian virus 40, polyoma virus, bovine papilloma virus, retrovirus or adenovirus. Ideally, the enhancer should be from a virus for which the host cell is permissive, i.e. which normally infects cells of the host type. Viral enhancers may be obtained readily from publically available viruses. The enhancer regions for several viruses, e.g., Rous sarcoma virus and simian virus 40, are well known. See Luciw et al., Cell 33:705–716 (1983). It would be a matter of routine molecular biology to excise these regions on the basis of published restriction maps for the virus in question and, if necessary, modify the sites to enable splicing the enhancer into the vector as desired. For example, see Kaufman et al, J. Mol. Biol., 159:601–621 (1982) and Mol. Cell Biol. 2(11):1304–1319 (1982). Alternatively, the enhancer may be synthesized from sequence data; the sizes of viral enhancers (generally less than about 150 bp) are sufficiently small that this could be accomplished practically.

Another element which should be present in the vector assembly is a polyadenylation splicing (or addition) site. This is a DNA sequence located downstream from the translated regions of a gene, shortly downstream from which in turn transcription stops and adenine ribonucleotides are added to form a polyadenine nucleotide tail at the 3' end of the messenger RNA. Polyadenylation is important in stabilizing the messenger RNA against degradation in the cell, an event that reduces the level of messenger RNA and hence the level of product protein.

Eucaryotic polyadenylation sites are well known. A concensus sequence exists among eucaryotic genes: the hexanucleotide 5'-AAUAAA-3' is found 11–30 nucleotides from the point at which polyadenylation starts. DNA sequences containing polyadenylation sites may be obtained from viruses in accord with published reports. Exemplary polyadenylation sequences can be obtained from mouse beta-globin, and simian virus 40 late or early region genes, but viral polyadenylation sites are preferred. Since these sequences are known, they may be synthesized in vitro and ligated to the vectors in conventional fashion.

The sequence which separates the polyadenylation site from the translational stop codon is preferably an untranslated DNA sequencs such as an unpromoted eucaryotic gene. Since such sequences and genes are not endowed with a promoter they will not be expressed. The sequence should extend for a considerable distance, on the order of up to about 1,000 bases, from the stop codon to the polyadenylation site. This 3' untranslated sequence generally results in an increase in product yields. The vector may terminate from about 30 bp downstream from the concensus polyadenylation sequence, but it is preferable to retain the 3' sequences found downstream from the polyadenylation site in its wild-type environment. These sequences typically extend about from 200 to 600 base pairs downstream from the polyadenylation site.

The presence of introns in the untranslated transcribed portion of the vector may increase product yields. Such introns may be obtained from other sources than either the host cells or the gene sources. For example, a hybrid inton comprising a 5' splice site from the second intron of the adenovirus tripartite leader and a 3' splice site from an immunoglobulin gene inserted downstream from transcription start site in the adenovirus major late promoter results in increased product yield.

In the preferred embodiment of the CSF cloning and expression vector there is a translational activator gene. Translational activators are genes which encode either protein or RNA products which affect translation of a desired mRNA. The best example is the adenovirus virus-associated (VA) gene (VAI) which is transcribed into a short RNA species that interacts with sequences in the 5' untranslated region of the adenovirus major late mRNAs (Thimmappaya et al., 1982 Cell 3 543). The necessary sequences for translational activation by VA RNA lie within the adenovirus late mRNA tripartite leader. The adenovirus tripartite leader is spliced together from noncontiguous regions of the adenovirus genome and is present on the 5' end of the adenovirus major late transcripts. VA RNA can interact to activate translation of mRNAs which contain the tripartite leader sequence. Thus, the preferred cDNA cloning and expression vector contains the spliced form of the tripartite leader, and the adenovirus VA genes.

These vectors can be synthesized by techniques well known to those skilled in this art. The components of the vectors such as enhancers, promoters, and the like may be obtained from natural sources or synthesized as described above. Basically, if the components are found in DNA available in large quantity, e.g. components such as vital functions, or if they may be synthesized, e.g. polyadenylation sites, then with appropriate use of restriction enzymes large quantities of vector may be obtained by simply culturing the source organism, digesting its DNA with an appropriate endonuclease, separating the DNA fragments, identifying the DNA containing the element of interest and recovering same. Ordinarily, a transformation vector will be assembled in small quantity and then ligated to a suitable autonomously replicating synthesis vector such as a procaryotic plasmid or phage. The pBR322 plasmid may be used in most cases. See Kaufman et al., op. cit.

The synthesis vectors are used to clone the ligated transformation vectors in conventional fashion, e.g. by transfection of a permissive procaryotic organism, replication of the synthesis vector to high copy number and recovery of the synthesis vector by cell lysis and separation of the synthesis vector from cell debris.

The vectors containing cDNA prepared from a cell that produces CSF activity are then transfected into E. coli and plated out on petri dishes at approximately 2000 colonies per dish. The colonies are lifted off onto a nitrocellulose filter and the filter is transferred to a new plate which is kept as a master. After growing these colonies, replicas are made and aligned with the original by careful marking so that sections of the replica filters can be identified with the corresponding portion of the master plate.

Each replica filter is cut into sections containing a predetermined number of colonies per section, preferably about 200–500 colonies per section. The colonies from each section are scraped into medium such as L-Broth, the bacteria collected by centrifugation and the plasmid DNA separated. The plasmid DNA from each section is transfected into a suitable host for expression of protein. The preferred synthesis vector herein is a mutant of the E. coli plasmid pBR322 in which sequences have been deleted that are deleterious to eucaryotic cells. See Kaufman et al., op. cit. Use of this mutant obviates any need to delete the plasmid residue prior to transfection. After growing the transfected cells, the medium is assayed for CSF activity. A positive assay indicates that a colony containing CSF/cDNA is on a particular section of a filter.

To determine which of the clones on the section of the original master filter contains CSF/cDNA, each clone on the filter section is picked and grown. The cultures are then placed in a matrix. Pools are prepared from each horizontal row and vertical column of the matrix. DNA samples are prepared from each pooled culture and transfected into the host cells for expression. Supernatants from these pools are assayed for CSF activity. One vertical column pool and horizontal row pool should produce CSF activity. The clone common to these pools will contain CSF/cDNA. If the matrix contains more than one positive clone, more than one column and row will be positive. In such case, further screening of a small number of clones may be necessary.

The CSF/cDNA is excised from the clones by restriction enzymes and can be sequenced by known techniques. It can be readily appreciated that the procedure described herein can be used to obtain CSF/cDNA from any source. The complete DNA sequence of a CSF/cDNA in accord with the invention is illustrated in FIG. 1 along with the predicted amino acid sequence of the translated CSF protein product.

The DNA sequence coding for a protein exhibiting CSF activity in accord with the present invention, such as illustrated in FIG. 1, can be modified by conventional techniques to produce variations in the final CSF protein which still have CSF activity in the assay tests described herein. Thus, for example, one, two, three, four or five amino acids can be replaced by other amino acids. Belgian Patent No. 898,016, which is incorporated herein by reference, describes one such typical technique for replacing cysteine by, e.g., serine.

CSF/cDNA in accord with this invention includes the mature CSF/cDNA gene preceded by an ATG codon and CSF/cDNA coding for allelic variations of CSF protein. One allele is illustrated in FIG. 1. Another allele that we discovered has a thymidine residue at position 365 instead of the cytosine residue illustrated in FIG. 1. The CSF protein of this invention includes the 1-methionine derivative of CSF protein (Met-CSF) and allelic variations of CSF protein. The mature CSF protein illustrated by the sequence in FIG. 1 begins with the sequence Ala.Pro.Ala.Arg . . . the beginning of which is depicted by an arrow after nucleotide number 66 in FIG. 1. The Met-CSF would begin with the sequence Met.Ala.Pro.Ala.Arg . . . The allele variation illustrated in FIG. 1 has a Thr at amino acid residue number 100 and can be referred to as CSF(Thr). Another variation has an Ile residue at position 100 and can be referred to as CSF (Ile). Purified CSF protein of the present invention exhibits a specific activity of at least $10^7$ units/mg of protein and preferably at least $4 \times 10^7$ units/mg when assayed with human bone marrow cells.

Host-vector systems for the expression of CSF may be procaryotic or eucaryotic, but the complexity of CSF may make the preferred expression system a mammalian one. Expression is easily accomplished by transforming procaryotic or eucaryotic cells with a suitable CSF vector. The DNA sequence obtained by the above described procedure can be expressed directly in mammalian cells under the control of a suitable promoter. Heterologous promoters well-known by those skilled in the art can be used. In order to express CSF in procaryotic or in yeast cells, the leader sequence (or secretory sequence) must be removed. The position of the codon for the N-terminus of the mature CSF protein is illustrated in FIG. 1. This can be done using standard techniques known by those skilled in the art. Once the desired CSF/cDNA clone is obtained, known and appropriate means are utilized to express the CSF protein, e.g. insertion into an appropriate vector, and transfection of the vector into an appropriate host cell, selection of transformed cells, and culture of these transformants to express CSF activity. The CSF protein thus produced may have a methionine group at the N-terminus of the protein (herein called Met-CSF). The mature proteins produced by procaryotic and eucaryotic cells will be otherwise identical in amino acid sequence, but the eucaryotic product may be glycosylated.

CSF protein expressed in appropriate procaryotic or eucaryotic cells can be recovered by purification and separation techniques known to those skilled in the art.

As aforesaid, the CSF protein in accord with the present invention can be used for treatment of myelo-suppression such as (symptomatic) granulocytopenia. For such use, a daily dosage of about 200 to 1000 ug per patient is typically indicated. The CSF protein is preferably injected into the patient intravenously in a suitable pharmacological carrier. Examples of such carriers include pharmacological saline and human serum albumin in saline.

The invention will be further understood with reference to the following illustrative embodiments, which are purely exemplary, and should not be taken as limitive of the true scope of the present invention, as described in the claims.

In the examples, unless otherwise specified, temperatures are in °C.

Restriction endonucleases are utilized under the conditions and in the manner recommended by their commercial suppliers. Ligation reactions are carried out as described by Maniatis et al., supra at 245–6, the disclosure of which is incorporated herein by reference, using the buffer described at page 246 thereof and using a DNA concentration of 1–100 ug/ml, at a temperature of 23° C. for blunt ended DNA and 16° C. for "sticky ended" DNA. Electrophoresis is done in 0.5–1 0.5% Agarose gels containing 90 mM Tris-borate, 10 mM EDTA. All radiolabeled DNA is labeled with $^{32}$P, whatever labeling technique was used.

By "rapid prep" is meant a rapid, small scale production of bacteriophage or plasmid DNA, e.g., as described by Maniatis et al., supra, at p. 365–373.

EXAMPLE A

Step 1. Mo Cell Line Cultures

Mo cells (ATCC CRL 8066) were grown routinely in Alpha (6% $CO_2$) or Iscove's (10% $CO_2$) medium containing 20% Fetal Calf Serum (FCS), 2 mM glutamine, 100 U/ml streptomycin and 100 ug/ml penicillin. The cells should be subcultured every 4–5 days. Cells are counted and seeded into Falcon T-175 flasks in 100–150 ml medium at density of 3–4×10$^5$ cells/ml. Cells will double in 20% FCS every 4–7 days. Growth rate is not constant and cells may sometimes appear to stop growing then go through bursts of growth. Mo cells can be grown in serum-free medium. Survival is much better when cells are not washed when transferred from FCS to serum-free medium. Optimal density in Serum-Free medium (SF) is 5×10$^5$ cells/ml. Cells will grow slightly (or at least maintain constant number) for 3 days in serum-free medium, and then should be fed 20% FCS for at least 4 days. This growth schedule (3 days SF, 4 days 20% FCS) can be repeated weekly if SF medium is required, with no apparent harm to the cells for several months.

Step. 2 Assays for CSF Activity

A. Bone Marrow Assay

Obtain fresh bone marrow. Break apart spicules by drawing through 20, 22, then 25 gauge needle. Dilute 1:1 with sterile phosphate-buffered saline (PBS) (room temperature) and layer over Ficoll-Paque (about 30 ml BM-PBS over 6 ml Ficoll). Spin at 1500 rpm for 40 minutes at room temperature. Remove fat and PBS layer and discard. Pipette off the light density layer. Wash 2× with PBS and count. Plate cells in RPMI (purchased from GIBCO as RPMI 1640) plus 10% HIFCS (heat inactivated FCS) for 3 hours to remove adherent cells.

Plating medium (make fresh):
20% FCS
0.3% agar dissolved in $H_2O$ cooled to 40° C.
2× Iscoves (1:1 v/v with Agar)
1% P/S final concentration of 100 ug/ml streptomycin, 100 U/ml penicillin
$10^{-4}$M alpha thioglycerol in 2× Iscoves from $10^{-2}$M stock
Cool agar to about 40°. Mix with other ingredients.
Cool in $H_2O$ bath to 37°–38° and hold at that temperature.

After 3 hours, pipette off the non-adherent cells. Spin and count. Add 2×10$^5$ cells/ml of plating medium and keep in controlled temperature water bath at 37°–38°. Add samples (e.g., medium from transfected cells; usually 10 ul sample) to the first row of wells of a microtiter plate in duplicate. Add 100 ul cell suspension to each well. Add additional 50 ul of cell suspension to each well in the first row. Mix thoroughly and transfer 50 ul of solution from the first row into the next row, etc. and continue 1:3 dilutions across plate. Wrap the plate in parafilm. Incubate 10–14 days at 10% $CO_2$, 37° C. in fully humidified atmosphere and score colonies.

To score the colonies, the total number of colonies that grow in each well is counted. In each assay, several wells are plated without including a sample (blank) to obtain a background colony count. The average number of colonies that grow in the blank wells is subtracted from the number of colonies found in each of the wells containing samples. One unit of CSF is the amount that will stimulate the formation of one colony above the background level per 10$^5$ human bone marrow cells (plated at 10$^5$ cells per ml) when the CSF concentration is sub-saturating. The sub-saturating concentration is determined by dilution and comparing the number of colonies at various dilutions to find the concentration just below the saturation level.

For this assay, the colonies containing granulocytes, monocytes or both types of cells are counted. The types of cells in the colonies are determined by picking colonies and staining individual cells.

B. KG-1 Cell Assay

KG-1 cells (Blood, Vol. 56, No. 3 (1980)) are grown in Iscoves medium+10% FCS passed 2× per week and seeded for each passage at 2×10$^5$ cells/ml. The cells are used for assay only between passage 30–35. The assay is the same as for bone marrow as described above, except the KG-1 cells are plated in agar mixture at 4×10$^3$ cells/ml.

The number of colonies growing in each well is determined and the background count is subtracted as in the Bone Marrow assay described above. One KG-1 CSF unit/ml is that concentration of CSF that will stimulate half of the maximum number (saturation) of KG-1 colonies to grow. The maximum number is obtained by including a saturating level of CSF in several wells.

Step 3. Construction of Vector p91023(B)

Figure 2:
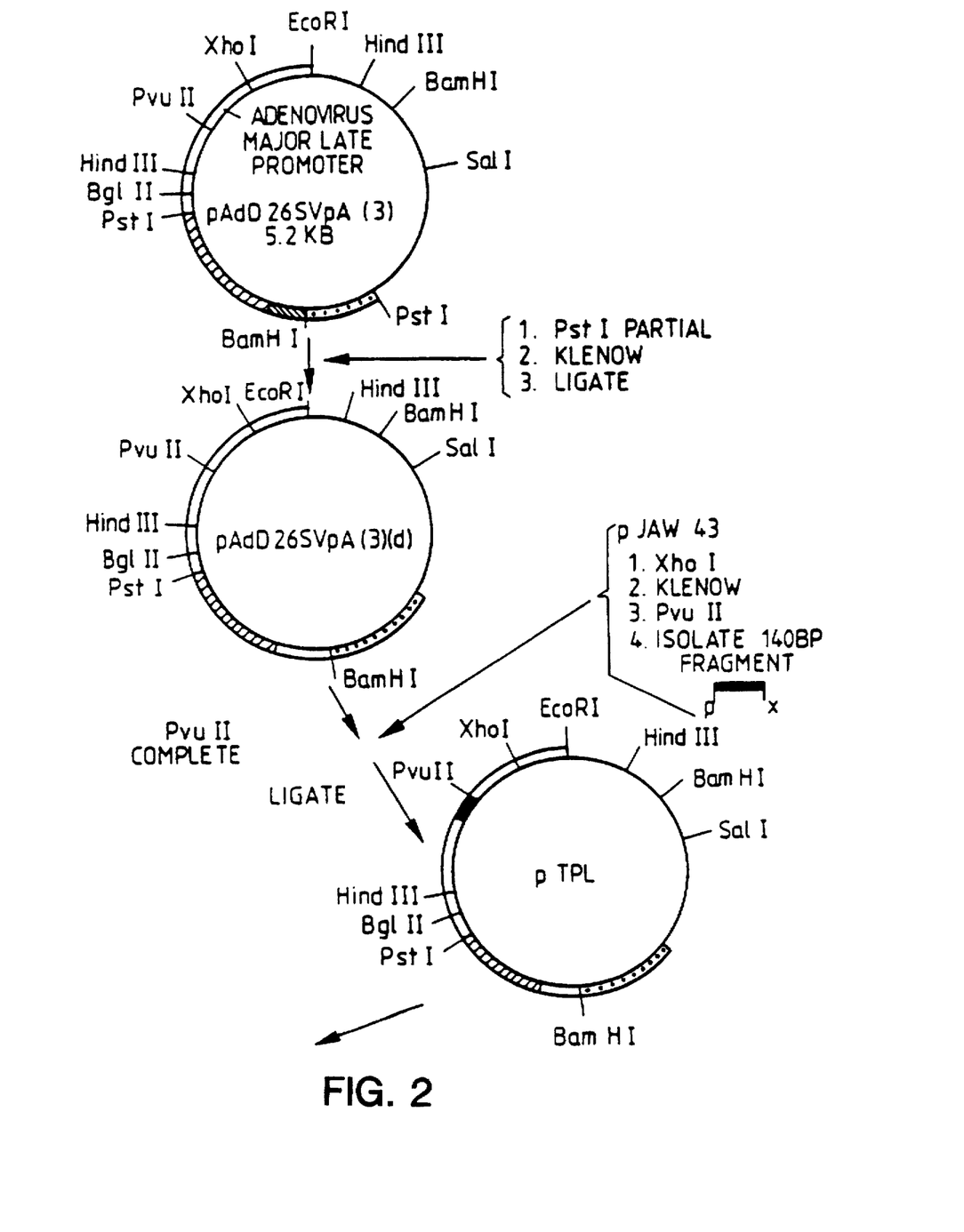
FIG. 2 is a schematic illustrating the preparation of plasmid pTPL from plasmid pAdD26SVpA(3).

The transformation vector was pAdD26SVpA(3) described by (Kaufman et al., Mol. Cell Biol. 2(11):1304–1319 [1982]. It has the structure illustrated in FIG. 2. Briefly this plasmid contains a mouse dihydrofolate reductase (DHFR) cDNA gene that is under transcriptional control of the adenovirus 2 (Ad2) major late promoter. A 5' splice site is included in the adenovirus DNA and a 3' splice site, derived from an immunoglobulin gene, is present between the Ad2 major late promoter and the DHFR coding sequence. The SV40 early polyadenylation site is present downstream from the DHFR coding sequence. The procaryotic-derived section of pAdD26SVpA(3) is from pSVOd (Mellon, P., Parker, V., Gluzman, Y. and Maniatis, T. 1981, Cell 27:279–288) and does not contain the pBR322 sequences known to inhibit replication in mammalian cells (Lusky, M., and Botchan, M. 1981, Nature (London) 293:79–81.

pAdD26SVpA(3) is converted into plasmid pCVSVL2 as illustrated in FIG. 2. pAdD26SVpA(3) is converted into plasmid pAdD26SVpA(3)(d) by deletion of one of the two PstI sites in pAdD26SVpA(3). This is accomplished by a partial digestion with PstI (using a deficiency of enzyme activity so that a subpopulation of linearized plasmids can be obtained in which only one PstI site is cleaved), then treatment with Klenow, ligation to recircularize the plasmid, transformation of *E. coli* and screening for deletion of the PstI site located 3' of the SV40 polyadenylation sequence.

The adenovirus tripartite leader and virus associated genes (VA genes) were inserted into pAdD26SVpA(3) (d) as illustrated in FIG. 2. First, pAdD26SVpA(3) (d) was cleaved with PvuII to make a linear molecule opened within the 3' portion of the first of the three elements comprising the tripartite leader. Then, pJAW 43 (Zain et al. 1979, Cell 16 851) was digested with Xho 1, treated with Klenow, digested with PvuII, and the 140 base pair fragment containing the second and part of the third leaders was isolated by electrophoresis on an acrylamide gel (6% in Tris borate buffer; Maniatis et al. [1982]supra). The 140 bp fragment was then ligated to the PvuII digested pAdD26SVpA(3) (d). The ligation product was used to transform *E. coli* to tetracycline resistance and colonies were screened using the Grunstein-Hogness procedure using a $^{32}$P labelled probe hybridizing to the 140 base pair fragment. DNA was prepared from positively hybridizing colonies to test whether the PvuII site reconstructed was 5' or 3' of the inserted 140 base pair DNA specific to the 2nd and 3rd adenovirus late leaders. In the correct orientation the PvuII site is on the 5' side of the 140 base pair insert. This plasmid is designated pTPL in FIG. 2.

The Ava II D fragment of SV40 containing the SV40 enhancer sequence was obtained by digesting SV40 DNA with Ava II, blunting the ends with Klenow fragment of Pol I, ligating Xho 1 linkers to the fragments, digesting with Xho 1 to open the Xho 1 site, and isolating the fourth largest (D) fragment by gel electrophoresis. This fragment was then ligated to Xho 1 cut pTPL yielding the plasmid pCVSVL2-TPL. The orientation of the SV40 D Fragment in pCVSVL2-TPL was such that the SV40 late promoter is in the same orientation as the adenovirus major late promoter.

To introduce the adenovirus virus associated (VA) genes into the pCVSVL2-TPL, first a plasmid pBR322 is constructed that contains the adenovirus type 2 Hind III B fragment. Adenovirus type 2 DNA is digested with Hind III and the B fragment is isolated after gel electrophoresis. This fragment is then inserted into pBR322 which has previously been digested with Hind III. After transformation of *E. coli* to ampicillin resistance, recombinants are screened for insertion of the Hind III B fragment and the inserted orientation is determined by restriction enzyme digestion. pBR322-Ad Hind III B contains the adenovirus type 2 Hind III B fragment in the orientation depicted in FIG. 3.

Figure 3:
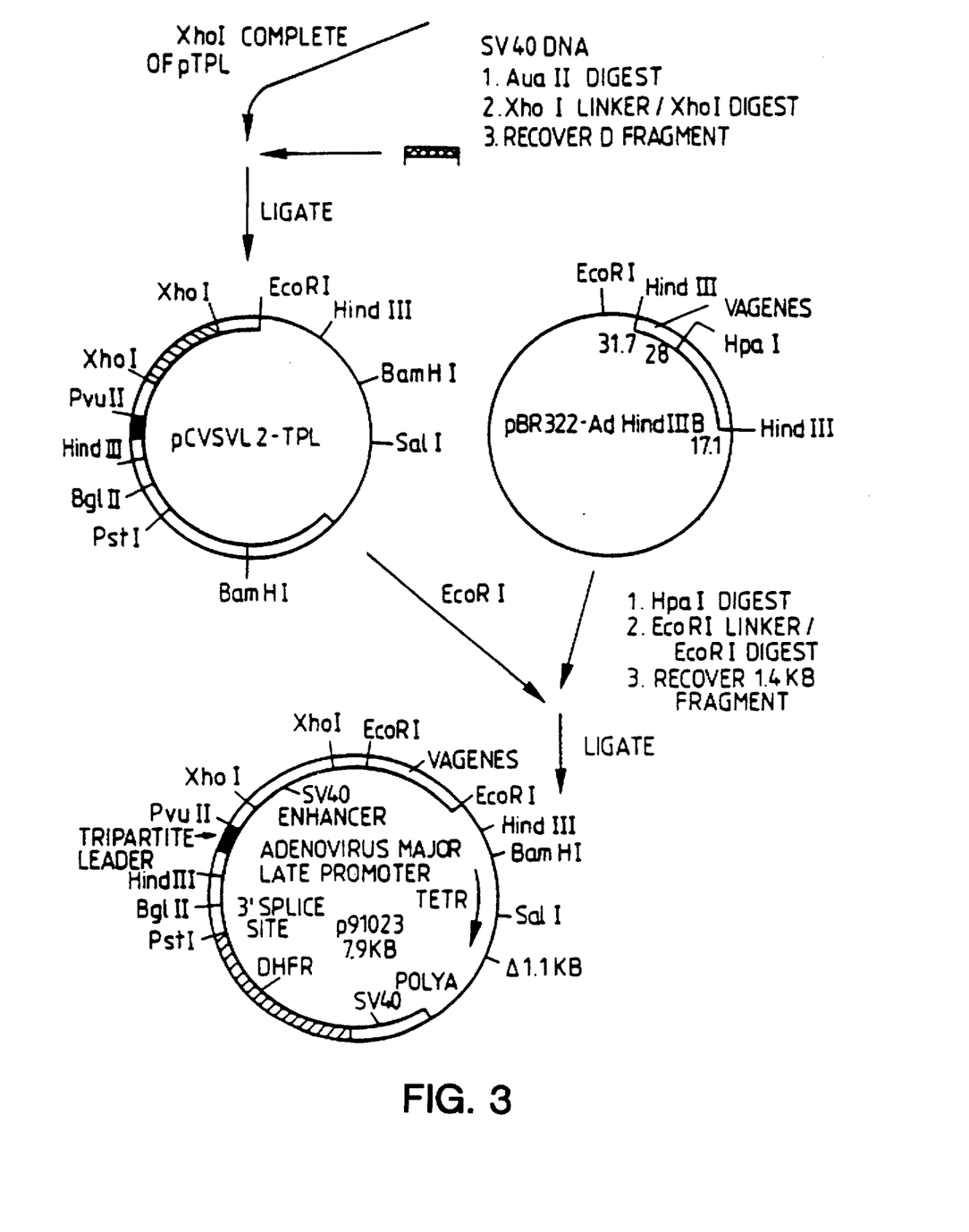
FIG. 3 is a schematic continuing from FIG. 2 and illustrating the preparation of plasmid p91023 from plasmid pTPL.
Figure 4:
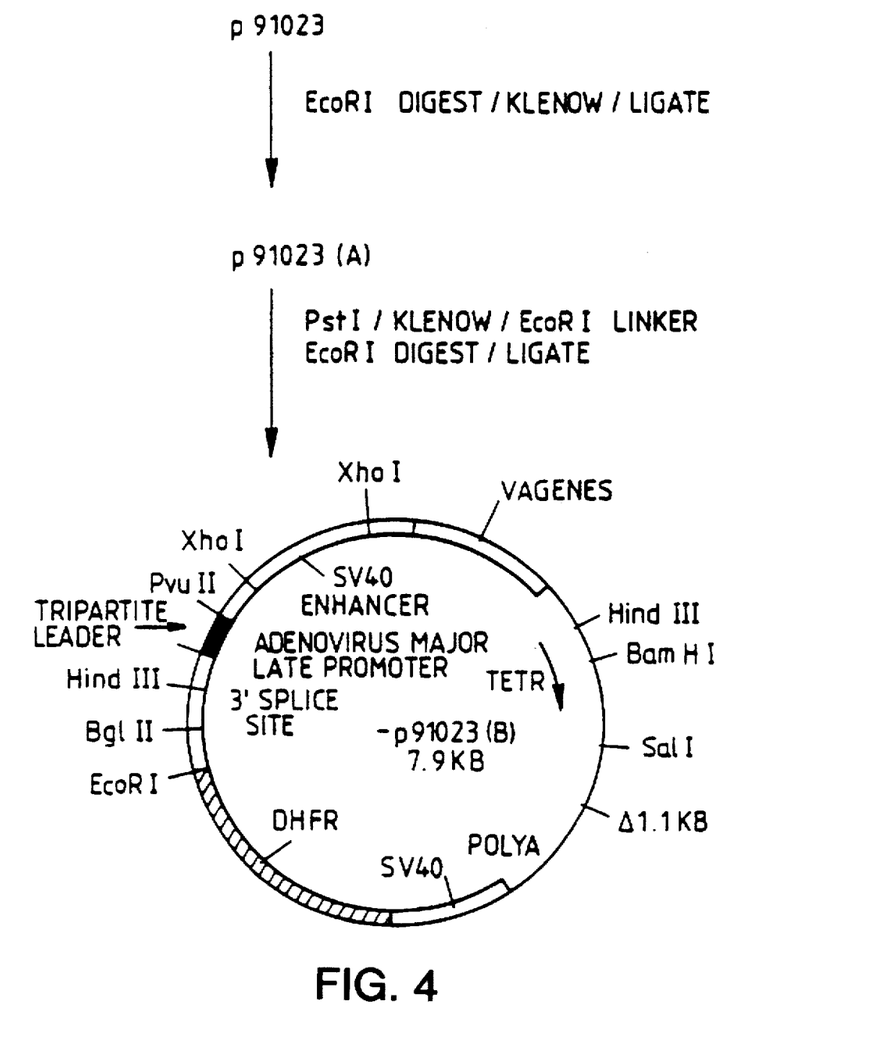
FIG. 4 is a schematic continuing from FIG. 3 and illustrating plasmid p91023(B).

As illustrated in FIG. 3, the VA genes are conveniently obtained from plasmid pBR322-Ad Hind III B by digesting with Hpa I, adding EcoRl linkers and digesting with EcoRl, and recovering the 1.4 kb fragment. The fragment having EcoRl sticky ends is then ligated into the EcoRl site of pTPL (which had previously been digested with EcoRl). After transformation of *E. coli* HB101 and selection for tetracycline resistance, colonies are screened by filter hybridization to a DNA probe specific to the VA genes. DNA is prepared from positively hybridizing clones and characterized by restriction endonuclease digestion. The product plasmid is designated p91023.

The 2 EcoRl sites in p91023 are removed. p91023 is cut to completion with EcoRl, generating two DNA fragments, one about 7 Kb and the other about a 1.3 Kb fragment containing the VA genes. The ends of both fragments are filled in using the Klenow fragment of PolI, and then both fragments i.e. 1.3 Kb, 7 Kb, are religated together. A plasmid p91023(A) containing the VA genes and similar to p91023 but deleted for the 2 EcoRl sites is identified by Grunstein-Hogness screening with the VA gene fragment, and by conventional restriction site analysis.

Then the single PstI site in p91023(A) is removed and replaced with an EcoRl site. p91023(A) is cut to completion with PstI, and then treated with Klenow fragment of PolI to generate flush ends. EcoRl linkers are ligated to the blunted PstI site of p91023(A). The linear p91023(A), with EcoRl linkers attached at the blunted PstI site is separated from unligated linkers and digested to completion with EcoRl, and then religated. A plasmid p91023(B) is recovered and identified to have a structure similar to p91023(A), but with an EcoRl site situated at the previous PstI site.

Step 4. Preparation of cDNA Library

Mo cells were induced for 16–20 hrs. with PHA and PMA to enhance their lymphokine production. Cells were plated at $5 \times 10^5$ cells/ml in Iscove's medium with 20% FCS, 0.3% (v/v) PHA and 5 ng/ml TPA. The cells were collected by centrifugation. The pelleted cells were resuspended in 20 ml of ice cold hypotonic lysis buffer (RSB buffer: 0.01M Tris-HCl, PH 7.4, 0.01M KCl, 0.0015M $MgCl_2$, 1 ug/ml cycloheximide, 50 units/ml RNAsin and 5 mM dithiothreitol). The cells were allowed to swell on ice for five minutes then were ruptured mechanically with 10 strokes of a tight fitting dounce glass homogenizer The homogenate was centrifuged at low speed (2000 RPM in a Beckman J6 centrifuge) to remove nuclei and unlysed cells. The supernatant was held on ice while the nuclear pellet was resuspended in 10 ml of RSB and re-centrifuged at low speed. This second supernatant was pooled with the first and the combined supernatants were centrifuged at low speed to remove residual contamination with nuclei and unlysed cells. The supernatant from this spin was brought to 0.15M KCl by addition of 2M KCl then centrifuged at high speed (25,000 RPM, Beckman Sw 28 rotor for 30 minutes) to pellet the membranes. The membrane pellet was carefully washed with cold RSB then resuspended in 12 ml of RSB containing 2M sucrose and 0.15M KCl. Two discontinuous gradients were prepared in Beckman SW41 centrifuge tubes by layering 6 ml of the membrane solution in 2M sucrose over 2 ml of RSB with 2.5M sucrose and 0.15M KCl. The tubes were filled to the top by overlaying with 2.5 ml of RSB containing 1.3M sucrose and 0.15M KCl. These gradients were spun for 4 hours at 27,000 RPM (Beckman, SW41 rotor) at 4° C. The membrane layer (at the interface between the 2.0M and 1.3M sucrose) was carefully removed from the side using an 18 gauge needle and syringe. The membrane fractions from the two gradients were pooled and diluted with 1 volume of distilled $H_2O$ then brought to 0.5% Triton X-100 and 0.5% sodium deoxycholate then extracted with an equal volume of phenol. The aqueous layer was re-extracted with a 1:1 mixture of phenol and chloroform and finally an equal volume of chloroform. Finally, the membrane bound RNA was precipitated by addition of NaCl to 0.25M and 2.5 volumes of cold ethanol and incubated overnight at −20° C. The precipitated RNA was collected by centrifugation (4000 RPM for 10 min. in the Beckman J-6 centrifuge) and was resuspended in 1 ml of distilled water. From $2 \times 10^9$ cells, approximately 1 mg of RNA was obtained The messenger RNA (mRNA) was isolated from the total RNA by chromatography on a 0.5 ml oligo dT-cellulose column. Briefly the RNA was heated to 70° C. for 5 min., quick chilled on ice, then diluted 5 fold with room temperature binding buffer (0.5M LiCl, 0.01M Tris-HCl, PH 7.4, 0.002M EDTA, and 0.1% SDS). The RNA in binding buffer was passed over the oligo dT-cellulose column equilibrated with binding buffer at room temperature. The column was washed with 5 ml of binding buffer then with 5 ul of 0.15M LiCl, 0.01M Tris-HCl pH7.4, 0.002M EDTA, and 0.1% SDS. Finally, mRNA was eluted with 2 ml of 0.01M Tris-HCl pH7.4, 0.002M EDTA, and 0.1% SDS. The mRNA was precipitated by addition of NaCl to 0.25M and 2.5 volumes of ethanol and incubation overnight at −20° C. The precipitated mRNA was collected by centrifugation (30,000 RPM for 30 minutes in a Beckman SW55 rotor). The tube was carefully drained and the mRNA pellet was resuspended in 50 ml of $H_2O$. The resuspended mRNA was brought to 0.25M NaCl then extracted 1 time with a 1:1 mix of phenol and chloroform then 3 times with chloroform. The mRNA was precipitated by the addition of 2.5 volumes of ethanol. The mixture was frozen and thawed several times in a dry ice/ethanol bath then centrifuged 15 min. in an Eppendorf centrifuge. The tube was carefully drained and the mRNA pellet was resuspended in 20 ul of distilled $H_2O$. The final yield was approximately 30 ug of mRNA.

First strand cDNA was prepared using standard methods. Briefly, 10 ug of membrane mRNA was diluted into a 100 ul cDNA synthesis reaction mixture containing 300 mM Tris pH 8.4, 140 mM KCl, 10 mM $MgCl_2$, 10 mM B-mercaptoethanol, 500 uM each of dATP, dGTP, dCTP and dTTP, 5 ug. of oligo-dT (phosphorylated and average size of 12–18) as primer, 150 uCi of $^{32}P$ dCTP (400 Ci/mmole) and 20 units of the ribonuclease inhibitor RNAsin. The reaction was initiated by addition of 100 units of reverse transcriptase and incubated for 30 minutes at 42° C. The reaction was stopped by addition of EDTA to 40 mM and the RNA was degraded by incubation for 20 min. at 65° C. in 0.2M NaOH. The base was neutralized by addition of 20 ul 2M Tris, pH 7.4. The reaction mix was then extracted with phenol/chloroform, back extracted with 50 ul 10 mM Tris pH 7.5, 1 mM EDTA (TE) and the aqueous phases were pooled. The first strand cDNA was converted to double stranded cDNA by incubation for 12 hours at 16° C. with 40 units of the Klenow fragment of DNA polymerase I in a 100 ul reaction containing 50 mM potassium phosphate, pH 7.4, 2.3 mM DTT, 2-mercaptoethanol, 10mM $MgCl_2$, 150 uMolar each of the 4 deoxynucleotide triphosphates and 25 uCi of $^{32}P$ dCTP. The reaction was stopped by extraction with phenol/chloroform and the unincorporated triphosphates were removed by passing the aqueous phase over a 1 ml sephadex G-50 column. The excluded fractions were pooled and ethanol precipitated.

The cDNA pellet was washed with cold ethanol then resuspended in 200 ul of 20 mM Tris pH 8.0, 1 mM EDTA, 80 uMolar S-adenosyl-Methionine, and 300 units of EcoRl methylase for 60 minutes at 37° C. The reaction was stopped by extraction with phenol/chloroform and the methylated cDNA was collected by ethanol precipitation.

The cDNA pellet was rinsed with 70% ethanol then resuspended in 200 ul S1 buffer (Maniatis et al) and incubated with 200 units of S1-nuclease at 30° C. for 30 minutes. The reaction was stopped by extraction with phenol/chloroform and the cDNA collected by ethanol precipitation.

The double stranded cDNA was blunted by incubation in 100 ul of 20mM Tris, pH 7.4, 50 mM NaCl, 10 mM 2 mercaptoethanol and 500 uMolar of all four deoxynucleotide triphosphates with 25 units of Klenow at room temperature for 30 minutes. The reaction was stopped by extraction with phenol/chloroform and the cDNA collected by ethanol precipitation.

The cDNA was ligated in 50 ul of T4 ligase buffer (Maniatis et al) with 500 pMoles of Rl linkers purchased from New England Biolabs (sequence: pCGGAATTCCG) using 2000 units of T4 ligase overnight at 16° C. The reaction was stopped by incubation at 70° for 20 minutes then diluted to 300 ul such that the final salt concentration was 0.1M NaCl, 10 mM, $MgCl_2$, 50 mM Tris-Cl, pH 7.4. The cDNA was then digested for 2 minutes at 37° with 700 units of EcoRl. The reaction was stopped by extraction with phenol/chloroform and the cDNA collected by ethanol precipitation. The pellet was resuspended in 50 ul of TE and passed over a 5 ml Cl-4B column. The excluded fractions were pooled and ethanol precipitated. The precipitated cDNA was electrophoresed through a 1% agarose gel in Tris acetate buffer in the presence of 1 ug/ml ethidium bromide. cDNA in the size range 500–4000 base pairs was isolated from the gel using the standard glass powder procedure. The eluted cDNA was extracted with phenol/chloroform, ethanol precipitated and the pellet (after an ethanol rinse) was resuspended in 50 ul of TE. The final yield was 100–500 ng of cDNA.

The preparation of the expression vector p91023(B) is described above. The EcoRl digested and phosphatase treated vector (500 ng) was ligated with 100 ng of cDNA in a 100 ul reaction (standard T4 ligase reaction) overnight at 16° C. The reaction was stopped by extracting with phenol/chloroform then the ligated cDNA was collected by ethanol precipitation after adding 5 ug of tRNA as carrier.

The ethanol precipitated DNA was rinsed with 70% ethanol then resuspended in 100 ul of TE. This DNA was used in 4 ul aliquots to transform *E. coli* MC1061 (4 ul in a 100 ul transformation). Each of the 25 transformations was spread onto a 150 mm petri dish with 1% agar, L-broth and 10 ug/ml tetracycline (Tet plate) and incubated overnight at 37°. Approximately 2000 colonies grew on each plate, resulting a total of about 50,000 colonies. After reaching approximately 0.5 mm in diameter, the colonies were transferred to nitrocellulose disks (137 mm) by carefully placing a dry filter on the surface of the plate then smoothly peeling off the filter. All of the colonies on the plate transferred to the filter which was then placed (colony side up) on a fresh Tet plate. After allowing the colonies to grow several hours, one replica was prepared from each of the filters by placing a fresh wetted filter exactly over the original filter, pressing them together, peeling them apart then returning each filter to a fresh Tet plate and incubating the plates overnight at 37°. Each replica was carefully marked such that it would be realigned with the original filter.

Step 5. Plasmid DNA Pool Preparation

Each of the 25 replica filters was carefully sectioned into eighths using a scalpel and noting the orientation of each eighth relative to the original master filter. The colonies were scraped from each section into 10 ml of L-Broth. The bacteria were collected by centrifugation (3000 RPM, 10 min., Beckman J-6 centrifuge) resuspended in 0.6 ml of 25% sucrose, 50M Tris-HCl pH 8.0 and converted to protoplasts by addition of 0.12 ml of 5 mg/ml lysozyme and incubation on ice for 5–10 min. The protoplasts were next incubated at room temperature for 10 min. following the addition of 0.125 ml of 0.5M EDTA then lysed by addition of 0.12 ml of 10% SDS in 50 mM Tris-HCl, pH 8.0. The lysate was mixed gently, incubated at room temperature for 15 min. then protein and chromosomal DNA precipitated by the addition of 0.3 ml of 5M NaCl. After incubation on ice for 15 min., the lysate was centrifuged in an Eppendorf centrifuge for 30 min. in the cold. The supernatant was carefully removed leaving behind the viscous DNA/protein pellet and was diluted by the addition of 2.5 ml H$_2$O. The mixture was extracted with 1 ml of phenol, the layers separated by centrifugation (10K for 10 min. in the Sorvall SS-34 rotor) and the aqueous layer removed to a fresh tube. DNA was precipitated by adding 0.5 ml of 5M NaCl and 7.5 ml of cold ethanol and freezing the mixture several times in a dry ice ethanol bath. The precipitate was collected by centrifugation (10K, 15 min. in the Sorvall SS-34), resuspended in 0.3 ml of 0.3M Sodium acetate and re-precipitated (in an Eppendorf tube) by the addition of 1 ml of ethanol. After 10–15 min. in a dry ice ethanol bath, the precipitated DNA was collected by centrifugation (5 min. in the Eppendorf) and the final pellet was resuspended in 100 ul of sterile TE (10 mM Tris pH8, 1 mM EDTA). From a typical preparation, 5–10 ug of plasmid DNA was obtained. Each preparation contained the DNA from 200–500 colonies on the original filter. A total of 200 DNA samples were prepared from the 25 filters.

Step 6. Isolating CSF Clone

Each of the DNA samples from Step 5 were separately transfected into M6 COS monkey cells as described below.

The M6 cells are grown routinely in DME (available from Gibco) plus 10% HIFCS, split twice a week at 1:6 dilution. Twenty-four hours after splitting 1:6 the M6 cells are ready for transfection. First, plates are aspirated and washed twice with 7 ml of serum-free (SF) DME. The DNA is dissolved in 0.1M Tris (pH 7.3) and added to DME medium containing 2 mM glutamine, 100 ug/ml streptomycin, 100 U/ml penicillin and 0.25 mg/ml DEAE Dextran totalling 4 ml with the Tris-DNA solution. The 4 ml of medium containing dissolved DNA is added to the plate containing M6 COS cells and incubated for 12 hours.

After incubation, the cells are rinsed once or twice with 7 ml SF DME. Then, 5 ml of DME with 10% HIFCS, 100 U/ml penicilin, 100 ug/ml streptomycin, 2 mM glutamine, and 0.1 mM chloroquin was added and the cells were incubated for 2½ hours.

After 2½ hours, rinse once with SF DME and add 10 ml DME+10% HIFCS/plate. After 30 hours aspirate media and feed 4 ml/plate DME+10% HIFCS. Harvest by removing the conditioned medium after 24–26 hours further incubation.

The conditioned medium from each transfection was assayed for CSF activity using the KG-1 assay. For each sample, positive for CSF activity, the clone on the original master filter responsible for the CSF activity had to be identified. For example, for one transfection positive for CSF activity, all of the colonies of the section of the original master filter from where the transfection DNA sample was derived, were picked. Some 320 of these colonies were picked into 3 ml of L-Broth plus 10 ug/ml tetracycline. The cultures were grown overnight. The 320 colonies were placed in an 18×18 matrix. Pools were prepared from each horizontal row and vertical column of the matrix (36 total pools) (note: the last horizontal row had only 14 clones). DNA samples were prepared from each pooled culture then used to transfect COS cells. The supernatants from these transfections were assayed using the KG-1 colony assay. Two positives were obtained from this set of transfections: one in a vertical column, the other a horizontal row. The culture common to these pools contained the CSF clone.

Twelve individual clones from this culture were isolated and miniprep DNA was prepared from 10 ml cultures in L-Broth as described above. 10 ul samples of DNA from these preparations were digested with EcoRl and the resulting DNA fragments analyzed by agarose gel electrophoresis. Nine of the twelve clones had a common approximately 750 base pair insert. The DNAs from four of these clones and the remaining three clones were introduced into M6 COS cells as described above. The supernatants from these transfections were assayed using the KG-1 assay as well as the bone marrow assay for CSF. The four clones which each contained the 750 bone pair fragment all directed the expression by the M6 COS cells of high levels of CSF activity as detected in either assay whle the other three clones did not. Thus, the coding region for CSF must be located within the 750 base pair insert.

The DNA sequence coding for CSF was removed from the transformation vector in the positive clone by digestion with EcoRl and sequenced using standard dideoxy sequencing methods after subcloning fragments into M13 vectors to obtain the sequence illustrated in FIG. 1. The plasmid, p91023(B)—CSF, that was first shown to direct CSF expression in COS cells has been designated pCSF-1. This plasmid has been deposited with the American Type Culture Collection in a strain of *E. coli*—MC1061 under the deposit number ATCC 39754.

Step 7. Expression of CSF Protein

M6 COS monkey cells transformed with vector p91023 (B) containing CSF/cDNA as isolated in Step 6 are grown as described in Step 6 to produce CSF protein in the culture medium.

Namely, one mg of this DNA (pCSF-1) was dissolved in 1 ml of 0.1M Tris, pH 7.3 and added to 600 ml of DME containing 2 mM glutamine, 100 U/ml streptomycin, 100 ug/ml penicillin (P/S) and 0.25 mg/ml DEAE Dextran (Molecular weight 500,000 from Pharmacia). The 600 ml of DNA DEAE Dextran solution is added to the M6 COS cells in the cell factory and incubated at 37° for 12 hours. After the incubation, the cells are rinsed once with 900 ml of SF DME then incubated for 2.5 hours with 600 ml of DME containing 0.1 mM chloroquin, 10% HIFCS, 2 mM glutamine and P/S. After aspirating the chloroquin containing medium, the cells are rinsed with SF DME and fed 1500 ml of DME with 10% HIFCS. After 30 hours the cells are washed with SF DME, the medium is replaced with 800 ml of SF DME and the transfected cells are allowed to condition the medium for 24 hours at 37° C. The conditioned medium is aspirated and replaced with another 800 ml of SF DME. The cells are allowed to condition this medium for 24 hours then the conditioned medium is collected. As soon as possible after harvesting, the conditioned media sample are concentrated 20 fold by pressurized ultrafiltration using the Amicon 2.5 liter chamber with the YM5 membrane (5,000 MW cutoff).

Step 8. Purification of Recombinant CSF

Two hundred ml of concentrated conditioned medium (from 4 liters of starting material—Step 7) was brought to 30% saturation of ammonium sulfate by addition of solid ammonium sulfate and the precipitated protein was removed by centrifugation. The supernatant was brought to 80% saturation of ammonium sulfate by adding more solid ammonium sulfate and the precipitated protein collected by centrifugation. The pellet was resuspended in 5 ml of 20 mM sodium citrate, pH 6.1, containing 1M NaCl. The dissolved protein was applied to a 2.5×100 cm column of Ultrogel AcA54 equilibrated in the same buffer. The CSF activity eluted from the column with an apparent molecular weight of 10 k Daltons or after about 90 ml. It has been observed that if the gel filtration is performed at low ionic strength, CSF activity is eluted from the column in two positions with apparent molecular weights of about 19 k Daltons and 38 k Daltons, suggesting that GM-CSF may readily form dimers.) The active fractions were pooled and brought to 0.15% TFA (by addition of 10% TFA) and applied to a Vydac C4 column (0.46×25 cm) equilibrated in 0.1% TFA. The column was developed with a linear gradient of 0–90% acetonitrile (1 ml/min., 340 ml total) in 0.1% TFA. The CSF activity eluted between 39 and 43% acetonitrile (Fractions 16–20). A 20 ul sample of Fraction 19 was analyzed by SDS polyacrylamide gel electrophoresis (13.5% gel as described by Lammli, Nature 227,680 (1970)). A single broad protein band with an apparent MW of 18–26 k Daltons was observed. The rather broad size range for CSF is a common feature of glycoproteins and is thought to reflect extensive but variable addition of carbohydrate. Protein from Fraction 19 was submitted to Edman Degradation using the Applied Biosystems gas phase microsequenator. From approximately 20 ug of protein applied, the sequence of the first 16 amino acids was obtained (A-P-A-R-S-P-S-P-S-T-Q-P-W-E-H). The high yield of this single protein sequence strongly suggested that the CSF protein in Fraction 19 had been purified to homogeneity. Bioassay indicated that Fraction 19 had $3\times10^7$ units per $A_{280}$ absorbance units. Since typical proteins in aqueous solution exhibit a range of extinction coefficients of 0.8 to 1.2 $A_{280}$ absorbance units per milligram of protein, the specific activity of the purified CSF is between about $1\times10^7$ and about $4\times10^7$ units/mg when assayed using the human bone marrow cell assay.

EXAMPLE B

CLONING GIBBON CSF

Step 1. Preparation of mRNA from Gibbon T-Cells

A sample of the gibbon T-Cell line designated UCD-MLA 144 was cultured for several weeks in RPMI 1640 (purchased from Gibco) and 20% fetal calf serum (FCS) until there was obtained $1\times10^9$ total cells. The cells were induced to product high levels of CSF by activation for 24 hours in the presence of 10 nanograms per ml 12-0-tetrdecanoyl phorbol 13-acetate (TPA) in RPMI 1640 plus 1% FCS. The cells were harvested by centrifugation (1000 rpm., 5 min.), washed once with phosphate buffered saline (PBS) and finally collected by centrifugation.

Membrane bound polysome (MBP) mRNA was prepared from these cells using the same procedure as described in Example A for the preparation of Mo cell RNA.

Step 2. First Strand cDNA Reaction 6 ug of MBP mRNA (from Step 1) was diluted into a 50 ul cDNA synthesis reaction mixture (see Example A—Step 4) and the reaction initiated by the addition of reverse transcriptase. After incubation for 30 minutes at 42° C., the reaction was stopped by addition of EDTA to 50 mM, and diluted with $H_2O$ to 100 ul. The mixture was extracted with phenol/chloroform and further extracted with chloroform. The cDNA/RNA hybrids were separated from unincorporated triphosphates by chromatography on a 2 ml Sepharose CL-4B column. The excluded fractions were pooled and the hybrids collected by ethanol precipitations. The final yield was 570 ng.

Step 3. Second Strand cDNA Reaction

The first strand cDNA pellet (Step 2) was resuspended in 50 ml of $H_2O$, and second strand synthesis carried out in a standard reaction mixture with E. coli Polymerase I, E. coli ligase, and RNAse H. The reaction was incubated overnight at 16° C. and then incubated for 1 hour at 37° C. The reaction was stopped by addition of EDTA and extracted with phenol/chloroform. The cDNA was separated from unincorporated triphosphates by chromatography on a Sepharose CL-4B column, the excluded fractions pooled and the cDNA collected by ethanol precipitation.

Step 4. Recombinant cDNA Preparation

The cDNA pellet (Step 3) was resuspended in 75 ul of $H_2O$. Homopolymeric C "tails" were added to the ends of the cDNA by adding 10 ul of the cDNA solution to a 25 ul standard reaction mixture with terminal transferase, and incubating at 30° C. for 5 minutes. The reaction was stopped by the addition of EDTA to 40 mM and heat inactivation at 68° C. for 10 minutes. 10 ng of this tailed cDNA was annealed with 50 ng of G-tailed pBR322 (purchased from NEN) in 10 ul of 10 mM Tris, pH 7.5, 1 mM EDTA, and 100 mM NaCl. The annealing reaction was incubated for 10 minutes at 68° C. and then for 2 hours at 57°.

Step 5. Bacterial Transformation

E. coli strain MC1061, was grown in L-broth, chilled on ice, harvested by centrifugation, and treated wth $CaCl_2$ to prepare them for transformation. 5 ul of the cDNA annealing reaction was then incubated with 200 ul of the $CaCl_2$-treated bacteria. Fifteen such transformations were performed, using all of the annealed cDNA, and spread on 15 cm, 1% agar L-broth plates containing 10 ug/ml tetracycline. Approximately 1000 colonies grew on each plate.

Step 6. Replica Plating 10,000 colonies from the transformation were each picked with a toothpick, transferred to fresh plates (500 per plate in a grid), and grown overnight at 37° C. The colonies were then lifted from each plate by pressing a dry nitrocellulose filter firmly over the surface of the plate. Two replica filters were prepared from each of these master filters. The master filters were stored at 4° C. and the replica filters treated with base, and baked to prepare them for hybridization.

Step 7. Preparation of $^{32}P$ Labelled Hybridization Probes

The cDNA insert from pCSF-1 was isolated by digestion with the restriction enzyme EcoRl, and electrophoresis in an agarose gel with Tris acetate and ethidium bromide. The band containing the cDNA fragment was cut from the gel and purified by the glass powder technique.

300 ng of the cDNA fragment was then added to 1 ul of 10×T4 DNA Polymerase Buffer (0.33M Tris Acetate, pH 7.9, 0.66M potassium acetate, 0.1M Magnesium acetate and 10 mM dithiothreitol), and 3 units of T4 DNA Polymerase (New England Biolabs), and diluted with water to 10 ul. After incubation for 5–10 minutes at 37° C., this mixture was combined with 1 ul 10×T4 DNA Polymerase Buffer; 1 ul of a 2 mM solution of each of dCTP, dTTP, dGTP; 10 ul of $^{32}PdATP$ (10uCi/ul, 3,000 Ci/mmole); and 3 units of Tr DNA Polymerase. The reaction was incubated for 20 minutes at 37° C. Then 1 ul of 2 mM dATP was added and the reaction incubated for an additional 10 minutes at 37° C.

The unincorporated triphosphates were separated from the labelled cDNA by chromatography on a Sephadex G100 column. A second probe was prepared from a synthetic oligonucleotide having the sequence:

ATC TGG CTG CAC AG which is complimentary to the amino terminus of the CSF coding region. This oligonucleotide was labelled with $^{32}P$ dATP at its 5' end using a standard polynucleotide kinase reaction.

Step 8. Isolation of CSF cDNA Clones

In a standard hybridization screening procedure, some 45 clones hybridized with the T4 labelled pCSF-1 cDNA. Of these, approximately 20 also hybridized to the labelled oligonucleotide probe. The coding region of one of these has been sequenced, and the sequence data revealed a number of base substitutions, some of which result in amino acid difference in the expressed protein. These differences are illustrated in FIG. 1 above the DNA sequence for the human CSF gene cloned in Example A.

EXAMPLE C

CLONING CSF FROM PERIPHERAL BLOOD LYMPHOCYTE mRNA

Step 1. mRNA Preparation from Peripheral Blood Lymphocytes

Peripheral blood lymphocytes were prepared from four plasmapheresis by-products (purchased from the Red Cross) by fractionation on a Ficoll-Hypaque gradient. The light density in RPMI-1640 in the presence of 5% fetal calf serum, 0.17% phytohemmaglutinin, and 10 ng/ml phorbal myristate acetate (PMA) at a density of $2 \times 10^6$ cells/ml (a total of $6 \times 10^9$ cells were obtained). The cells were harvested by centrifugation (1000 rmp, 5 min.), washed once with phosphate buffered saline (PBS) and finally collected by centrifugation. Cytoplasmic RNA was prepared by a gentle lysis procedure in which the cells were resuspended in 50 ml cold Triton lysis buffer (140 mM NaCl, 1.5 mM $MgCl_2$, 10 mM Tris, pH 8.6, 0.5% Triton X-100) with 10 mM dithiothreitol (DTT) and 50 units/ml RNAsin (purchased from Biotec). This lysate was divided into 2 equal parts and each part was layered over a 10 ml cushion of lysis buffer containing 20% sucrose. The cell nuclei were removed by centrifugation in the cold (4° C., 400 rpm for 5 minutes). The upper layer (cytoplasmic extract) was carefully removed and sodium dodecylsulfate (SDS) was added to a final concentration of 1%. This solution was extracted twice with an equal volume of phenol chloroform (1:1 mixture) and the RNA was precipitated by adding 2.5 volumes of cold ethanol. The precipitated RNA was collected by centrifugation (15 min. at 4000 rpm) and resuspended in 0.01M Tris, pH 7.5, 1 mM EDTA, 0.25M NaCl (TE buffer plus 0.25M NaCl) and reprecipitated by addition of 2.5 volumes of cold ethanol. Finally, the RNA was collected by centrifugation and resuspended in 5 ml of $H_2O$. The final yield was 7.5 mg.

Messenger RNA was isolated from the total cytoplasmic RNA by selection on oligo dT cellulose. 2.5 mg of total RNA was heated to 65° for five minutes. NaCl was added to 0.5M and the RNA was allowed to cool to room temperature. This RNA was passed over a one ml column of oligo dT cellulose equilibrated in TE+0.5 m NaCl (binding buffer). Unbound RNA was removed by washing the column extensively with binding buffer. Bound messenger RNA was eluted with 3 ml of $H_2O$ and precipitated by addition of 0.2 ml of 4M NaCl and 2.5 volumes of cold ethanol. The precipitated mRNA was collected by centrifugation (30 minutes at 25,000 rpm). The final pellet (approximately 100 ug) was resuspended in 50 ul of $H_2O$.

Step 2. First Strand cDNA Reaction 20 ug of PBL mRNA was diluted into a 50 ul cDNA synthesis reaction containing 100 mM Tris, pH 8.4, 140 mM KCl, 10 mM $MgCl_2$, 10 mM 2-mercaptoethanol, 400 uM each of dATP, dGTP, dCTP, and dTTP, 5 ug of oligo-dT (average size 12-18) as primer, 25 uCi of 32PdCTP (400 uCi/mmole) and 20 units of the ribonuclease inhibitor RNAsin. The reaction was initiated by addition of 60 units of reverse transcriptase at 37° C. and incubated for 30 minutes at 42° C. The reaction was stopped by addition of EDTA to 40 mM and extracted with an equal volume of $H_2O$ saturated phenol. The phenol phase was back extracted with 50 ul of TE buffer. The aqueous phases were pooled. The cDNA/RNA hybrids were separated from unincorporated triphosphates by passing the pooled aqueous phase over a 5 ml Sepharose CL-4B column (purchased from Sigma), equilibrated with TE. The fractions that were excluded from the column were pooled, brought to 250 mM NaCl and the nucleic acids precipitated by addition of 2.5 volumes of cold ethanol. The hybrids were collected by centrifugation for 30 minutes at 40,000 rpm. The final pellet (2.5 ug of cDNA) was resuspended in 50 ul of $H_2O$.

Step 3. Second Strand cDNA Reaction

Second strand cDNA was synthesized by the combined action of the enzymes *E. coli* DNA Polymerase I, *E. coli* DNA ligase and *E. coli* RNAse H. The reaction mixture (50 ul) contained 20 mM Tris, pH 8.0, 4 mM $MgCl_2$, 1.2 mM EDTA, 25 uM NAD, 100 uM each of dATP, dGTP, dCTP, and dTTP; and 50 uCI $^{32}PdCTP$ (3,000 Ci/mmole). The reaction was performed by adding 3 units DNA polymerase I, 0.5 units DNA ligase, and 0.75 units of RNAse H and incubating at 16° for 18 hours, then at 37° for 1 hour, and then stopped by adding EDTA to 40 mM and extracted with an equal volume of phenol. The phenol phase was back extracted with 50 ul TE, the aqueous phases pooled, and the cDNA was separated from the unincorporated triphosphates by chromatography on a Sepharose CL-4B column as described above for the first strand. Based on incorporation of $^{32}P$, the first strand cDNA was quantitatively converted to a double-stranded form.

Step 4. Recombinant cDNA Preparation

Homopolymeric C "tails" were added to the ends of the cDNA by gently heating 400 ng of cDNA in a 50 ul reaction mixture containing 1 mM 2-mercaptoethanol, 1 mM $COCl_2$, and 9 units of terminal deoxynucleotidyl transferase at 30° C. for five minutes. The reaction was stopped by the addition of EDTA to 40 mM and heating to 68° C. for 10 minutes. 200 ng of this tailed cDNA was annealed with 500 ng of G-tailed pAT153 (purchased from Amersham) in 100 ul of 10 mM Tris, pH 7.5, 1 mM EDTA, and 100 mM NaCl. The annealing reaction was performed at 57° for 2 hours after a 5 minute preincubation at 68° C.

Step 5. Bacterial Transformation

The cDNA annealing reaction product was used directly to transform the *E. coli* strain MC1061. A fresh colony of bacterial cells was used to inoculate 50 ml of L-broth and grown for several hours until the optical density at 550 nm was 0.25. The cells were chilled on ice and harvested by centrifugation (2000 rpm for 10 min.). The pellet was resuspended in 10 ml of cold 0.1 m $CaCl_2$ and allowed to sit on ice for 10 minutes. The cells were collected by centrifugation (2000 rpm for 5 minutes) and resuspended in 2 5 ml of 0.1M $CaCl_2$. 10 ul of the cDNA annealing reaction was then incubated with 200 ul of $CaCl_2$-treated bacterial for 30 minutes on ice and then for 2 minutes at 37° C., followed by addition of 0.8 ml of L-broth and final incubation for 30 minutes at 37° C.

Twenty of these transformations were performed, utilizing all of the annealed cDNA. Each transformation mixture was spread onto 1% Agar L-broth plates (15 cm diameter) containing 10 ug/ml tetracycline. From the twenty transformations a total of 20 such plates were spread and incubated overnight at 37° C. On the average approximately 1,500 bacterial colonies grew on each plate for a total of 30,000 clones.

Step 6. Replica Plating

The original colonies growing on each plate were transferred to 137 mm nitrocellulose filters by pressing a dry filter on top of the colonies and lifting them off the plate. Two identical replicas were prepared from each original filter by standard replica plating methods, in which each original filter was carefully placing methods, in which each original filter was carefully placed colony side up on a sterile square of filter paper (Whatman 3 MM) resting on a square piece of glass. A new pre-wetted nitrocellulose filter was carefully aligned on top of the master filter, covered with a second sterile square of filter paper and the complete sandwich then pressed together firmly with a second piece of glass. The sandwiched filters were numbered and 3 pinholes were punched through them asymmetrically so that they could be exactly aligned again in the future. The replica was then removed from the master and placed colony side up on a new tetracycline-containing L-broth agar plate. A second replica was immediately prepared in identical fashion. Each master filter was returned to a plate and all of the plates were incubated at 37° for several hours until the bacterial colonies had reached approximately 1 mm in diameter. The original master filters were stored at 4° C. and the replicas prepared for hybridization as described below.

Step 7. Preparation of Filters for Hybridization

Each replica filter (Step 6) was placed colony side up on filter paper (Whatman 3 MM) soaked in 0.5M NaOH, 1.5M NaCl for seven minutes. The filters were transferred to neutralization filter papers, soaked in 1 m Tris, pH 7.5, 1.5M NaCl, for 2 minutes and then transferred to a second set of neutralization filters for 5–10 minutes. Finally, the filters were placed on filters soaked in SSC buffer (0.015M Sodium Citrate, 0.15M NaCl, pH 7.4) for five minutes, air-dried and baked in vacuo at 80° C. for 1–2 hours.

Step 8. Isolation of CSF cDNA Clones

Duplicate filters were probed with the radioactively labelled pCSF-1 cDNA insert, prepared as described above in Example B. Some 20 colonies hybridized with the cDNA. Twelve of these were picked from the master filter and grown overnight in L-broth for further analysis. Restriction enzyme digests (Pst 1) of DNA samples (rapid prep) from these clones indicated that 3 were nearly full length. One of these has been sequenced. The sequence of the CSF coding region of this clone was identical to the corresponding sequence of pCSF-1 (i.e. having a T at position 365-CSF (Ile)). Therefore, physiological functions of CSF may be severalfold. In the bone marrow, this lymphokine can stimulate proliferation and differentiation of effector cells for host defense while, in the periphery, new and existing cells can be activated. In a localized immunological response CSF can retain circulating neutrophils in or away from areas of inflammation. Inappropriate localization and/or activation of neutrophils can be involved in the pathophysiology of a variety of immune-mediated disorders such as rheumatoid arthritis.

This invention has been described in detail, including the preferred embodiments thereof. However, it will be appreciated that those skilled in the art, upon consideration of this specification, may make modifications and improvements within the spirit and scope of the invention.

For instance, it has been shown that murine CSFs activate neutrophils. Thus, it would be expected that the primate CSFs of the present invention will also activate neutrophils.

What is claimed:

1. A method of treating a mammal having myelo-suppression, comprising the step of:

administering to said mammal an effective amount of GM-CSF protein to stimulate production of granulocytes.

2. The method of claim 1, wherein said GM-CSF protein is administered by intravenously injecting said mammal with a composition comprising said GM-CSF protein in a pharmacological carrier.

3. A method of treating a mammal to increase the number of circulating granulocytes, said method comprising the step of:

administering to said mammal an effective amount of GM-CSF protein to increase the number of circulating granulocytes.

4. The method of claim 3, wherein said GM-CSF protein is administered to a mammal with cancer following chemotherapeutic or irradiation treatment of said cancer.

* * * * *

UNITED STATES PATENT AND TRADEMARK OFFICE
CERTIFICATE OF CORRECTION

PATENT NO. : 5,720,952

DATED : February 24, 1998

INVENTOR(S) : STEVEN C. CLARK ET AL.

It is certified that error appears in the above-identified patent and that said Letters Patent is hereby corrected as shown below:

On title page, item

[75] INVENTORS

"Gordon C. Wong" should read --Gordon G. Wong--

COLUMN 1

Line 58, "et al" should read --et al.--.

COLUMN 3

Line 52, "CSF. The" should read --CSF; the--.
Line 53, "for the" should read --the--.

COLUMN 4

Line 61, "such" should read --such a--.

COLUMN 6

Line 2, "publically" should read --publicly--.

COLUMN 8

Line 45, "above described" should read --above-described--.
Line 47, "well-known" should read --well known--.

UNITED STATES PATENT AND TRADEMARK OFFICE
CERTIFICATE OF CORRECTION

PATENT NO. : 5,720,952

DATED : February 24, 1998

INVENTOR(S) : STEVEN C. CLARK ET AL.  Page 2 of 3

It is certified that error appears in the above-identified patent and that said Letters Patent is hereby corrected as shown below:

COLUMN 9

Line 11, "limitive" should read --limitative--.
    Line 23, "0.5-1 0.5%" should read --0.5 - 1.5%--.

COLUMN 12

Line 29, "homogenizer" should read --homogenizer.--
    Line 63, "obtained" should read --obtained.--.

COLUMN 14

Line 36, "resulting" should read --resulting in--.

COLUMN 15

Line 54, "culture" should read --culture and--.

COLUMN 16

Line 6, "whle" should read --while--.

COLUMN 18

Line 8, "57°." should read --57°C.--.

UNITED STATES PATENT AND TRADEMARK OFFICE
CERTIFICATE OF CORRECTION

PATENT NO. : 5,720,952

DATED : February 24, 1998

INVENTOR(S) : STEVEN C. CLARK ET AL.

It is certified that error appears in the above-identified patent and that said Letters Patent is hereby corrected as shown below:

<u>COLUMN 20</u>

Line 37, "2 5 ml" should read --2.5 ml--.
    Line 57, "placing methods, in which each original" should be deleted.
    Line 58, "filter was carefully" should be deleted.
    Line 66, "agan" should read --again--.

<u>COLUMN 21</u>

Line 21, "colonies" should read --colonies were--.

Signed and Sealed this

Eighteenth Day of April, 2000

Attest:

Q. TODD DICKINSON

*Attesting Officer*    *Director of Patents and Trademarks*